United States Patent
Webb et al.

(10) Patent No.: US 8,679,852 B2
(45) Date of Patent: Mar. 25, 2014

(54) PARTICULATE MATTER GENERATOR FOR USE WITH AN EMISSIONS CONTROL DEVICE AGING SYSTEM

(75) Inventors: Cynthia C. Webb, San Antonio, TX (US); John W. Miller, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 113 days.

(21) Appl. No.: 13/076,621

(22) Filed: Mar. 31, 2011

(65) Prior Publication Data

US 2012/0252130 A1 Oct. 4, 2012

(51) Int. Cl.
*G01N 1/28* (2006.01)

(52) U.S. Cl.
USPC ......... 436/160; 436/155; 436/159; 73/114.69

(58) Field of Classification Search
USPC ........... 436/181, 37, 155, 159, 160; 73/23.33, 73/114.69; 60/276
See application file for complete search history.

(56) References Cited

U.S. PATENT DOCUMENTS

| 7,741,127 B2 | 6/2010 | Johnston Bartley et al. |
| 2007/0289290 A1* | 12/2007 | Bartley et al. ................... 60/282 |
| 2008/0053195 A1* | 3/2008 | Matter et al. ................. 73/28.01 |

OTHER PUBLICATIONS

The Application of Woodward's Diesel Burner System to a Low Temperature Duty Cycle Application Using Tenneco's ELIM-NOx SCR System. Feb. 28, 2009 Michael B. Riley, Ed VanDyne.*

* cited by examiner

*Primary Examiner* — Krishnan S Menon
*Assistant Examiner* — Dwan A Gerido
(74) *Attorney, Agent, or Firm* — Chowdhury & Georgakis PC; Ann C. Livingston

(57) ABSTRACT

A particulate matter generator implemented as a "mini-burner", and used in conjunction with a larger test system for the specific purpose of enhancing the particulate matter content of exhaust gas. The exhaust stream of the larger system is supplemented with exhaust from the mini-burner to produce exhaust with desired particulate matter characteristics. The exhaust gas may then be used for various test purposes, such as testing emissions control devices.

10 Claims, 2 Drawing Sheets

PARTICULATE MATTER GENERATOR FOR USE WITH AN EMISSIONS CONTROL DEVICE AGING SYSTEM

TECHNICAL FIELD OF THE INVENTION

This invention relates generally to systems and methods for simulating exhaust gas produced by an internal combustion engine, and more particularly to such systems and methods that produce exhaust containing particulate matter.

BACKGROUND OF THE INVENTION

Numerous test methods have been devised to simulate aging of devices that treat exhaust emissions from automobile engines and other internal combustion engines. Some test systems are "engine-based", and use actual internal combustion engines to generate exhaust gas into the emissions control device being tested. However, engine-based systems can be inconsistent and expensive to operate.

Because of difficulties associated with using engines, burner-based test systems have been developed to produce exhaust and otherwise simulate conditions under which exhaust after treatment devices must perform. Examples of burner-based test systems for testing emissions control devices are described in U.S. Pat. Nos. 7,625,201, 7,277,801, 7,140,874, and 6,983,645, all assigned to Southwest Research Institute.

The specific task of generating particulate matter (PM) as a component of exhaust is beginning to gain significance for testing emissions control devices. Durability testing, regeneration strategy, and product development have led to a need for systems that provide accelerated PM loading. Some existing systems produce only carbon-based PM. Other systems generate PM comprising oil ash and other desired constituents. An example of a system developed specifically for exhaust containing PM is described in U.S. Pat. No. 7,741,127, to Bartley, et al, entitled "Method for Producing Diesel Exhaust with Particulate Material for Testing Diesel Engine After treatment Devices".

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

The following description is directed to various embodiments of an exhaust gas generation system used for generating exhaust gas that contains particulate matter (PM). A common application of these systems is for testing an emissions control device, which directly receive the exhaust gas output of the system. The systems simulate the exhaust produced by an engine in real world operation. In all embodiments, a special PM generator ("mini-burner") is used to add particulate matter to the exhaust stream upstream the emissions control device.

Burner-Based Particulate Matter Exhaust Generator

Figure 1:
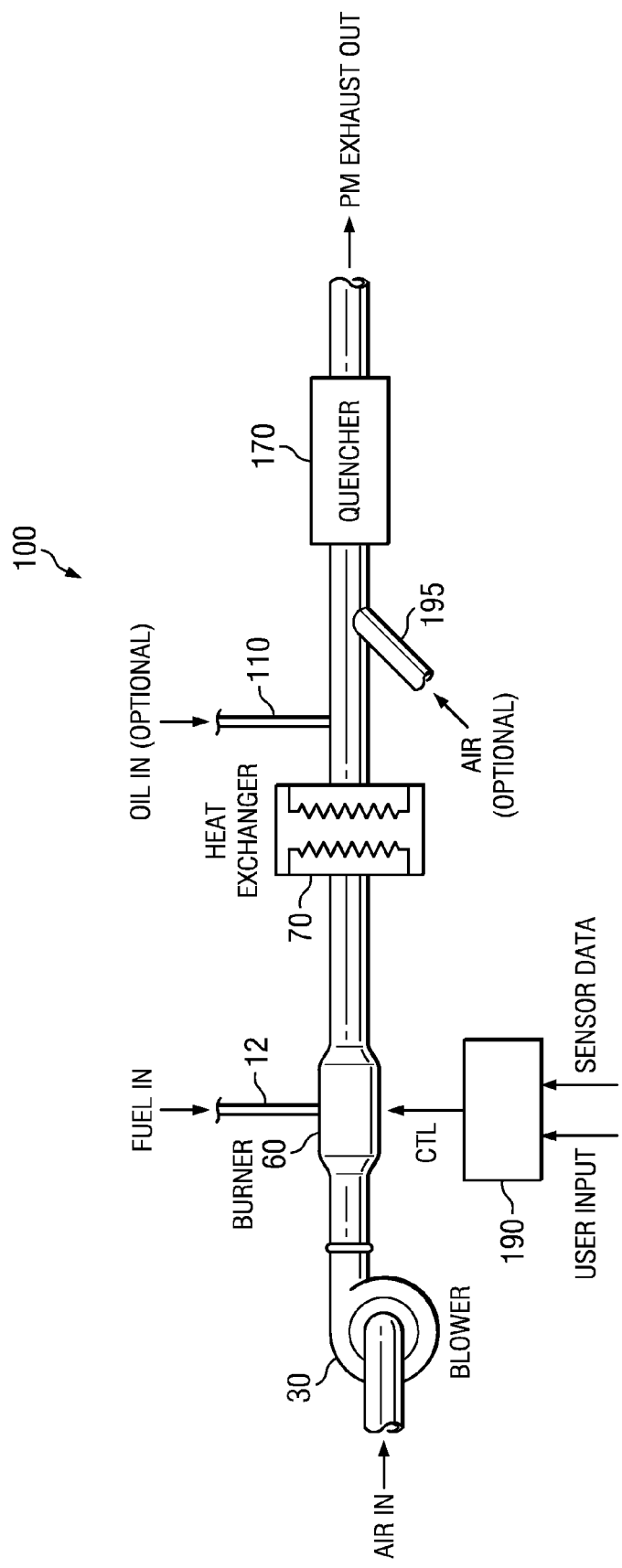
FIG. 1 illustrates a burner system for generating exhaust that contains particulate matter (particulate matter generator).

FIG. 1 illustrates a burner-based particulate matter (PM) generator 100 suitable for use with the methods of the present invention. PM generator 100 is especially suited for generating exhaust containing particulate matter (PM) having desired characteristics.

More specifically, PM generator 100 produces a flow of exhaust gas with a composition and temperature corresponding to the exhaust flow produced by a given type of engine. The exhaust gas is produced by combusting fuel, and contains particulate matter (PM) having desired characteristics. PM generator 100 provides control over the rate and composition of the major PM constituents (such as carbon, soluble organic fractions, and oil ash). The effect of extended driving conditions and elevated temperatures on the composition of the exhaust gas and its PM can be simulated. The system can also simulate the effects of various additives and contaminants.

The basic elements of PM generator 100 are a blower 30, burner 60, heat exchanger 70, and quencher 170. As illustrated in FIG. 1, other optional features of PM generator 100 are an oil injector 110, which injects lubricants or additives into the exhaust stream. Also, an air injector 195 may be used to inject secondary air into the exhaust line.

The methods described herein are directed to use of PM generator 100 in conjunction with some other exhaust generation system, as a way of supplementing that system's output by providing a desired amount of particulate matter. For this purpose, PM generator 100 may be appropriately described as a "mini burner" system, relative to the scale of the larger system with which it is used.

An air blower 30 draws ambient air and exhausts a pressurized stream of air. The volume of air supplied is set by adjusting a valve (not shown) or by other means to produce a desired flow rate of air.

Burner 60 combusts fuel and air at a specified air-fuel ratio. Via a fuel line 12, fuel is delivered to a fuel spray nozzle in the burner 60. Burner 60 may be used to combust various types of fuels for internal combustion engines. Examples of such fuels are gasoline, synthetic gasoline, diesel, biodiesel, liquefied fuel produced from coal, peat or similar materials, ethanol, methanol, compressed natural gas, or liquefied petroleum gas. The exhaust is provided with a specified air-to-fuel ratio.

An example of a suitable burner 60 is a swirl-stabilized burner capable of producing continuous combustion at a specified mode (lean, rich or stoichiometric). Such as burner has a plenum chamber and a combustion tube, divided by a swirl plate. Air and fuel are separately introduced into the burner 60. Air is delivered to the plenum chamber, then through the swirl plate into the burner tube. The swirl plate is equipped with a fuel injector. The mixture of gas and air are combusted with the aid of at least one spark igniter, which may be placed through the wall of the combustion tube of burner 60. An example of a suitable burner is described in U.S. Pat. No. 7,741,127, referenced above.

The exhaust from the burner 60 is routed to a heat exchanger 70. The heat exchanger 70 may be of any conventional design known to a person of ordinary skill in the art. Various air-cooled or liquid-cooled designs may be used to implement heat exchanger 70. Heat exchanger 70 cools the exhaust gas to reach (or assist in reaching) a desired exhaust gas temperature.

At some point on the exhaust stream, illustrated in FIG. 1 as downstream from the heat exchanger 70, the exhaust gas is routed past an optional oil injector 110, which may be used to introduce a precisely controlled amount of lubricating oil into the exhaust stream. The oil injector provides an atomized oil spray comprising oil droplets with a sufficiently small diameter to vaporize and oxidize the oil. For generating exhaust gas with desired PM composition, the oil injector 110 is typically used to inject engine lubricant or additives commonly found in such lubricants. Regardless of whether it is oil or additives to be injected, injector 110 is referred to herein as an "oil" injector.

At some other point in the exhaust stream, illustrated in FIG. 1 as downstream the heat exchanger 70, secondary air injector 195 supplies air (or any other gas) into the exhaust flow. As explained below, for generating exhaust gas with desired PM composition, the air injector 120 is typically used to inject oxygen into the exhaust gas. Regardless of whether it is air or oxygen or some other gas to be injected, injector 195 is referred to herein as an "air" injector.

Quencher 170, is used to lock the PM to whatever form it is in when it reaches quencher 170. Typically, this is accomplished by injecting an inert gas into the exhaust stream. Other quenchers might use ice or cool water or water vapor to chill the exhaust.

Control unit 190 provides a means to control operating parameters of system 100, such as ignition, air assist to the fuel injector, auxiliary air, fuel feed, blower air feed, and oil injection. An example of a suitable control unit 190 is a processor-based system having hardware and software appropriate for the data acquisition, processing, and control signal generation described herein. The level of sophistication of control unit 190 may vary from simple embedded controller type devices to computers with sophisticated user interface programming.

Control unit 190 is in communication with various sensors (not shown), which collect data representing a number of operating conditions of PM generator 100. Examples of such data are: the mass air flow in the system, the air/fuel ratio (linear and EGO), and the exhaust gas temperature at various points on the exhaust flow line. The data measured by the sensors is transmitted to control unit 190.

Control unit 190 controls the parameters associated with system 100 by using various valves and actuators. Examples of control output parameters are power to the blowers and fuel pump, activation of fuel injectors, burner spark, oil injection, and auxiliary air.

In operation, control unit 190 receives signals representing system temperatures, mass air flow for the burner air, and the burner air to fuel ratio. These measurements are converted to data, and the measured data is the basis for calculating operating conditions such as total exhaust flow and burner air to fuel ratio.

U.S. Pat. No. 7,741,127, referenced in the Background, describes a specific example of a burner system capable of generating similar PM as PM generator 100. That patent is incorporated by reference herein.

Generation of Particulate Matter in Exhaust

Particulate matter (PM) is formed during the combustion process and during the subsequent travel of the exhaust gases within the exhaust system. The PM generally comprises carbon, metal, adsorbed organic compounds (i.e., hydrocarbons), and varying amounts of sulfates, nitrates, and combinations thereof. The formation of PM can be simulated by using various forms of carbon power (carbon black) or by operating the burner under fuel-rich conditions. PM may also contain varying amounts of sulfate from fuel and oil sulfur, and a soluble organic fraction originating mostly from lubricating oil.

Not only is PM a composite material, but its components themselves are responsible for PM formation and its characteristics. The process by which the particulates are formed is one of nucleation and agglomeration.

The particulates can be very fine. The primary (nuclei) carbon particles have an average diameter from about 0.01 microns to about 0.08 microns, while the aggregates have an average diameter from about 0.08 microns to about 1 microns.

System 100 can generate the same PM as generated by a given engine. The composition of the PM in an engine's exhaust also depends on engine operating conditions. The actual composition of the particulates also depends on the thermodynamic conditions in the diesel exhaust and the particulate collection system being used. For example, under normal engine operating conditions, particles can become coated with adsorbed and condensed high molecular weight organic compounds. Because PM originates in the engine cylinder as a result of high pressure and temperature, and is affected by fuel to air ratio in various regions of the combustion chamber, it is not trivial to re-create PM other than by means of an actual diesel compression ignition engine. A feature of system 100 is that it may be programmed and operated to generate a diesel exhaust comprising a desired composition and size of diesel particulates.

Referring to FIG. 1, burner 60 is used to generate an initial PM precursor. Burner 60 is typically operated rich of stoichiometry to induce incomplete fuel and oil combustion, and thereby to provide nascent PM. By appropriately programming control unit 190, the fuel can be doped with lubricating oil or lubricating oil additives. In the same manner, the sulfur content of the fuel and/or oil can be controlled, as well as ash-forming components of the oil.

The multiphase mixture from burner 60 flows through heat exchanger 70 for cooling. The rate of cooling is controlled, such as by varying the residence time in the heat exchanger 70, to achieve desired nucleation and agglomeration of the PM.

Downstream of heat exchanger 70, the exhaust is "matured", using either or both the oil injector 110 or the oxygen injector 195. Injector 195 is used to inject gases, such as air or oxygen. In particular, injector 195 may be used to raise the oxygen content to simulate the oxygen content of diesel exhaust. The air or oxygen may be injected where the exhaust gas is at a predetermined temperature. A suitable temperature at the point of injection is less than 650 degrees C., and more typically, 500 degrees C. or less.

The in-exhaust oil injector 110 can be used either upstream or downstream of the gas injector 195. Oil or oil additive components injected via injector 110, as compared to being added to the fuel, is less combusted and can be used to simulate the part of the PM formation process that does not directly result from combustion in the engine combustion chambers. This oil injection is used primarily to modify the soluble organic fraction of the PM.

Oil formulations contain materials that form ash as part of their "base" formulation. By doping the base formulation with high concentrations of these materials, the ash formulation rate can be manipulated and/or accelerated.

Heat exchanger 70 receives the exhaust from burner 60. As stated above, the exhaust may be cooled to any desired temperature. Quencher 170 "sets" the PM composition as described above.

Use of PM Generator to Supplement Larger Burner Systems

As indicated above, PM generator 100 may be implemented as a "mini burner" and used in conjunction with a larger test system for the specific purpose of enhancing the PM content of the exhaust. In some test systems, without the use of PM generator 100, PM generation is difficult due to elevated temperatures and lean conditions. For such systems, their exhaust stream may be supplemented with exhaust from mini-burner 100 to produce exhaust with desired PM characteristics. Using PM generator 100 as a mini-burner and shifting the task of PM generation from the main system to the PM generator, permits the main exhaust generation system to be smaller and less complex.

Figure 2:
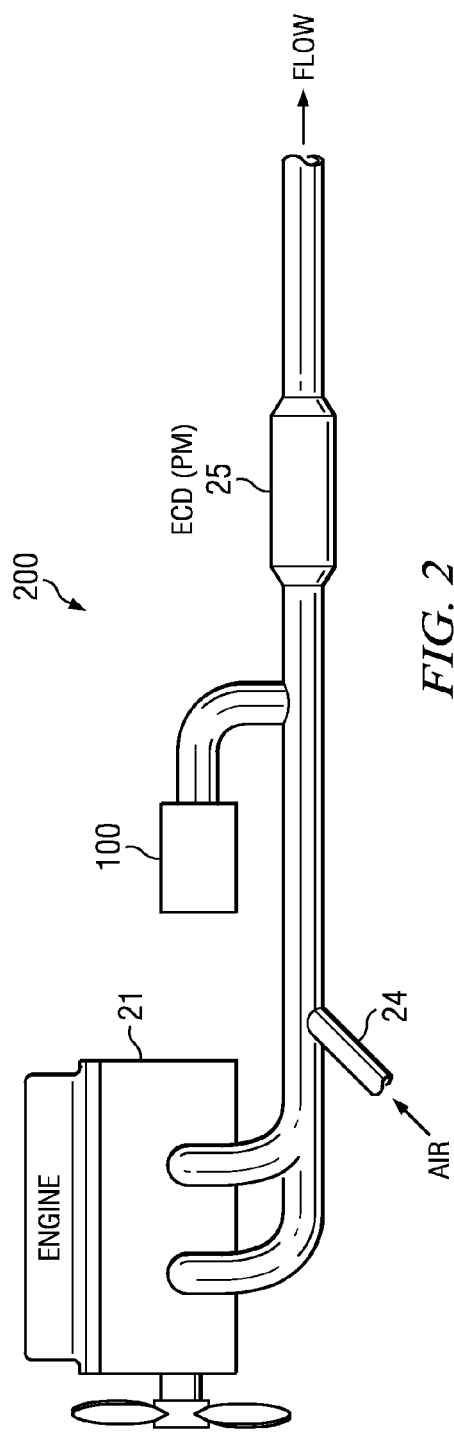
FIG. 2 illustrates an example of an engine-based exhaust generation system having a particulate matter generator.
Figure 3:
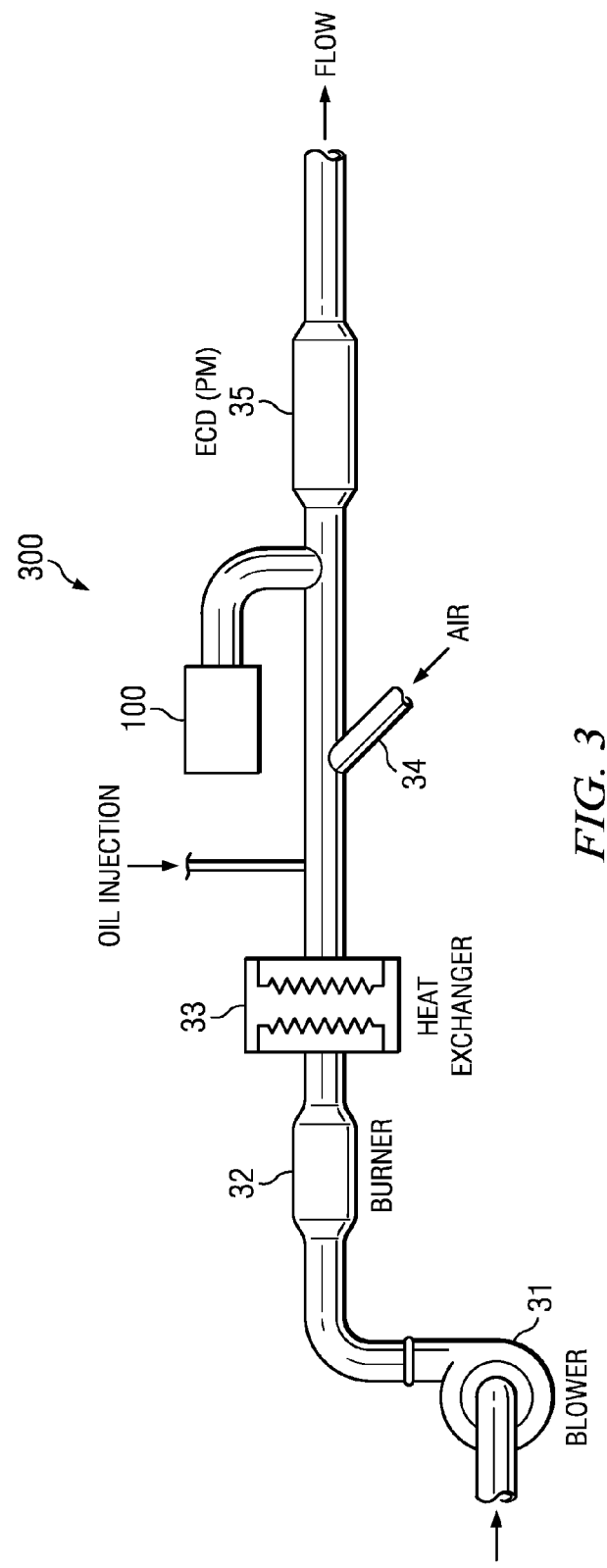
FIG. 3 illustrates an example of a burner-based exhaust generation system having a particulate matter generator.

In both FIGS. 2 and 3, PM generation is used as a mini-burner for a larger scale "main" system. FIG. 2 illustrates exhaust generator 100 used as a "mini burner" with an engine-based test system 200. FIG. 3 illustrates exhaust generator 100 used as a mini-burner with a burner-based test system 300.

In the embodiments of FIGS. 2 and 3, the combined exhaust from the main system 200 or 300 and the PM generator 100 is directly provided to an emissions control device. Examples of devices that might be tested in this manner are devices that remove or oxidize PM, such as diesel oxidation catalysts, gasoline particulate filters, selective catalytic reduction devices, and EGR particulate filters. However, exhaust with a desired PM content may also be collected and used to evaluate the effects of PM fouling on other devices such as EGR coolers, turbochargers, intake throttles, sensors, EGR valves, and brakes.

In the engine-based system 200, an engine is used to produce exhaust. Such systems are sometimes referred to as "engine aging stands". The exhaust from the engine 21 is delivered to the emissions control device 25. The output of the PM generator 100 is introduced into the exhaust flow line somewhere between the engine 21 and the emissions control device 25. An air injector 24 could be used to inject air or other gas into the exhaust stream.

The burner-based system 300 may have elements similar to those of the PM generator: a blower 31, burner 32, heat exchanger 33, and air injector 34. An example of a suitable burner-based test system 300, apart from mini-burner 100 is described in U.S. Pat. No. 7,140,874, entitled "Method and Apparatus for Testing Catalytic Converter Durability", to Ingalls, et al., assigned to Southwest Research Institute, and incorporated by reference herein.

System 200 and system 300 may operate as a "high dilution" systems. In system 300, the total exhaust flow comprises the output of burner 32 and dilution air from air injector 34. The total exhaust flow is controlled by varying these two sources of gas. Although not explicitly shown in FIG. 3, heat exchanger 33 may be configured to receive hot exhaust from burner 32, and thereby recover heat energy from the exhaust to preheat the dilution air.

What is claimed is:

1. A method of generating exhaust gas that contains a desired amount of particulate matter, comprising:
   using an engine to generate exhaust gas into a main exhaust flow line that directs the exhaust gas to an emissions control device or a collector;
   using a particulate matter generator to generate supplemental exhaust gas having desired particulate matter characteristics;
   wherein the particulate matter generator has at least a burner for receiving fresh air and fuel and combusting the fresh air and fuel to produce exhaust gas and nascent particulate matter in the exhaust gas; a heat exchanger for cooling the exhaust gas downstream of the burner; an oil injector for modifying a soluble organic fraction of the particulate matter; and a quencher for locking the composition of the particulate matter;
   wherein in the particulate matter generator is positioned on a branch line off the main exhaust flow line, such that the burner does not receive exhaust from the engine
   wherein the quencher operates by injecting an inert gas into the output of the heat exchanger;
   operating the particulate matter generator at a rich air-fuel ratio, using a predetermined air-fuel ratio calculated to produce a desired concentration of particulate matter in the exhaust gas;
   introducing the output of the particulate matter generator from the branch line into the main exhaust flow line; and
   delivering the combined exhaust from the engine and the exhaust from the particulate matter generator to the emissions control device or collector;
   wherein the particulate matter generator generates substantially all particulate matter in the exhaust gas, such that the combined exhaust has the substantially the same concentration of particulate matter as is generated by the particulate matter generator; and
   wherein the concentration of particulate matter in the exhaust gas is of a predetermined amount for testing the emissions control device or collector.

2. The method of claim 1, further comprising doping the fuel with sulfur compounds.

3. The method of claim 1, further comprising doping the fuel with lubricating oil or at least one lubricating oil additive.

4. The method of claim 1, further comprising using an oil injector, located between the heat exchanger and the quencher, to inject a pre-determined amount of engine lubricant or additive into the exhaust gas, thereby providing a pre-determined amount of soluble organic fraction into the exhaust gas.

5. The method of claim 1, further comprising using an oil injector, located between the heat exchanger and the quencher, to inject a pre-determined amount of additive into the exhaust gas, thereby providing ash in the exhaust gas.

6. A method of generating exhaust gas that contains a desired amount of particulate matter for testing one or more exhaust aftertreatment devices, comprising:
   using a burner-based test stand to generate exhaust gas into a main exhaust flow line; wherein the burner-based test stand has at least a main burner for combusting air and fuel and generating a primary exhaust gas flow;
   operating the main burner at a lean air-fuel ratio;
   using a particulate matter generator to generate supplemental exhaust gas having a desired particulate matter characteristics;
   wherein the particulate matter generator has at least a mini-burner for receiving air and fuel and combusting the air and fuel to produce a secondary flow of exhaust gas and nascent particulate matter in the secondary flow of exhaust gas; a heat exchanger for cooling the exhaust gas downstream of the mini-burner; an oil injector for modifying a soluble organic fraction of the particulate matter; and a quencher for locking the composition of the particulate matter;
   wherein in the particulate matter generator is positioned on a branch line off the main exhaust flow line, such that the burner does not receive exhaust from the engine;
   operating the particulate matter generator at a rich air-fuel ratio, using a predetermined air-fuel ratio calculated to produce a desired concentration of particulate matter in the exhaust gas;
   wherein the quencher operates by injecting an inert gas into secondary flow of exhaust gas;
   introducing the output of the particulate matter generator from the branch line into the main exhaust flow line; and
   delivering the combined exhaust from the test stand and the exhaust from the particulate matter generator to the one or more aftertreatment devices;

wherein the particulate matter generator generates substantially all particulate matter in the exhaust gas, such that the combined exhaust has the substantially the same concentration of particulate matter as is generated by the particulate matter generator; and wherein the concentration of particulate matter in the exhaust gas is of a predetermined amount for testing at least one of the aftertreatment devices;

wherein the main burner generates other exhaust gas components for testing at least one of the aftertreatment devices.

7. The method of claim 6, further comprising doping the fuel with sulfur compounds.

8. The method of claim 6, further comprising doping the fuel with lubricating oil or at least one lubricating oil additive.

9. The method of claim 6, further comprising using an oil injector to inject a pre-determined amount of engine lubricant or additive into the secondary flow of exhaust gas, thereby providing soluble organic fraction into the secondary flow of exhaust gas.

10. The method of claim 6, further comprising using an oil injector to inject a pre-determined amount of additive into the secondary flow of exhaust gas, thereby providing ash in the secondary flow of exhaust gas.

* * * * *